United States Patent
Fleischer et al.

(10) Patent No.: US 6,915,678 B2
(45) Date of Patent: Jul. 12, 2005

(54) OZONE SENSOR OPERATING ACCORDING TO THE WORK FUNCTION MEASUREMENT PRINCIPLE

(75) Inventors: Maximilian Fleischer, Hohenkirchen (DE); Hans Meixner, Haar (DE); Bernhard Ostrick, Berlin (DE); Roland Pohle, Herdweg (DE); Elfriede Simon, Munich (DE); Martin Zimmer, Munich (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/422,713

(22) Filed: Apr. 25, 2003

(65) Prior Publication Data

US 2004/0025568 A1 Feb. 12, 2004

(30) Foreign Application Priority Data

Apr. 26, 2002 (DE) .......................................... 102 18 810

(51) Int. Cl.⁷ .............................. G01N 7/00; H01L 23/58
(52) U.S. Cl. ...................... 73/31.05; 73/31.02; 257/253
(58) Field of Search ............................ 73/31.01, 31.02, 73/31.03, 31.05, 23.2; 422/82.01, 88, 90, 92; 204/412, 415; 257/253

(56) References Cited

U.S. PATENT DOCUMENTS

| | | | | |
|---|---|---|---|---|
| 4,238,758 A | * | 12/1980 | Suzuki ........................ 257/253 |
| 4,812,221 A | * | 3/1989 | Madou et al. ............... 204/412 |
| 5,200,633 A | * | 4/1993 | Dickert et al. .............. 257/253 |
| 5,425,869 A | * | 6/1995 | Noding et al. .............. 204/418 |
| 5,879,631 A | * | 3/1999 | Wewers et al. .............. 422/98 |
| 2002/0131898 A1 | * | 9/2002 | Fleischer et al. ......... 422/82.01 |
| 2003/0121781 A1 | * | 7/2003 | Prohaska et al. .......... 204/424 |

FOREIGN PATENT DOCUMENTS

| | | | |
|---|---|---|---|
| DE | 2947050 A | * | 5/1981 |
| DE | 4028062 A | * | 3/1992 |
| DE | 198 49 932 A1 | | 5/2000 |

OTHER PUBLICATIONS

T. Doll et al., "Ozone detection in the ppb range with work function sensors operating at room temperature", Sensors and Actuators B 34 (1996) 506–510.

A. Fuchs, "Ozonsensorik mit Feldeffekttransistoren", Institute fur Physic, Fakultat fur Elektrotechnik, Universitat der Bundeswehr Munchen, 1999.

* cited by examiner

*Primary Examiner*—Michael Cygan
(74) *Attorney, Agent, or Firm*—Young & Thompson

(57) ABSTRACT

An ozone sensor has an ozone-sensitive layer containing an ozone-sensitive material which is encapsulated in a polymer or in a polymer mixture or is coated by at least one polymer or polymer mixture. Advantages result from a longer service life of the ozone-sensitive materials which, because of their high hygroscopic properties, would not be stable without encapsulation or coating. Furthermore, a polymer matrix can be selectively used as a filter or in order to eliminate interfering influences.

23 Claims, 3 Drawing Sheets

OZONE SENSOR OPERATING ACCORDING TO THE WORK FUNCTION MEASUREMENT PRINCIPLE

FIELD OF THE INVENTION

The invention relates to an ozone sensor having at least one gas-sensitive material, in which the sensor signal is generated according to the work function change principle. Halogenide compounds, for example, are used as sensitive materials.

BACKGROUND OF THE INVENTION

It is known that metal halogenides, which are in fact ozone-sensitive, exhibit a strong hygroscopic behavior. This leads to a major problem when metal halogenides are used as gas-sensitive layers.

The strong hygroscopic behavior of ozone-sensitive halogenide salts such as potassium iodide (KI) or sodium iodide (NaI), for example, means that a gas-sensitive layer produced from these salts is unstable and results in the dispersion of this layer upon reaction with water. Consequently, the sensitive layer loses its structure, which leads to a loss of sensitivity culminating in total insensitivity. Previously, this meant that sodium iodide could not be used as a gas-sensitive layer. Furthermore, the gas absorption of the layers with ozone leads to a transformation of the sensitive layer material and hence to a change in the surface morphology. Studies revealed that the ozone treatment led after a certain period of time to the occurrence of layer instabilities, including shrinking of the material, agglomeration of the salt crystals, and separation of the layers. For this reason the layer becomes increasingly damaged already after, for example, six weeks in service, which is associated with a continuous reduction in sensitivity. As a result of the strong hygroscopic behavior, the ozone measurements based on metal halogenides exhibit a high cross-sensitivity at least to humidity. This means that the measurement or sensor signal changes with different humidity concentrations analogously to the ozone concentration and therefore leads to a falsely positive ozone signal or else too high an ozone signal is simulated. For this reason a correction of the ozone signal relative to the response to humidity or else to other interfering influences is essential.

Gas-sensitive layers are not suitable for use in gas sensor technology if they do not exhibit sufficient stability. The previously described ozone-sensitive materials usually exhibit a life of about 12 weeks. However, for practical application in the end consumer sector it is essential that the sensor exhibits a longer service life and also a lower cross-sensitivity to humidity.

Previous layer preparations for ozone-sensitive layers were based in particular on vapor deposition on a substrate of a sensor body, a technique which is described in particular in [1]. Layers of this type exhibit the above-described problems in particular.

To solve these problems, measures such as those described in particular in [2] have already been taken previously.

For example, an attempt was made to overcome the problems by variation of the ozone-sensitive salts. When KI is used in a humid atmosphere, the strong hygroscopic behavior of the material and the resulting formation of potassium hydroxide (KOH) lead to dispersal of the layer. No improvements could be achieved in this regard by the use of other possible ozone-sensitive salts, for example other alkali halogenides (NaI, LiI) or alkaline earth halogenides ($CaI_2$, $SrI_2$). Firstly, some of these halogenides are no longer stable in air; secondly, some of these compounds exhibit a much stronger hygroscopic behavior than KI itself. As a result, layer preparation is precluded from the outset.

Another measure to improve the problems cited consists in pretreatment of the substrate surfaces with lithium hydroxide (LiOH). Pretreatment of the $SiO_2$ surface with concentrated LiOH solutions causes free bonding points to be activated at the substrate surface. Following intensive ozone treatment it was shown that although a somewhat stronger bonding of the KI to the substrate surface could be achieved than, for example, on a substrate coated with platinum, the surface coating was porous.

Artificial roughening of the surfaces, for example, was used to enlarge the total surface area, with the aim of achieving improved bonding and coating of the surface. When this is done, however, the layer is similarly damaged following ozone treatment and some of the KI crystals migrate to the outside.

A further improvement was anticipated through the use of porous silicon, onto which KI was applied by vapor deposition. In a subsequent treatment with ozone, it was revealed that a layer prepared by this method exhibited the most stable surface adhesion. However, since the silicon has to be metallized, the good adhesion properties are reduced due to the flattening of the pores.

Another variation on eliminating the cross-sensitivity to humidity consists in the use of a separate humidity measurement by means of an external humidity sensor in order to correct the actual gas sensor signal.

SUMMARY OF THE INVENTION

The object of the invention is to provide an ozone-sensitive layer that can be used for an ozone sensor and that is dimensionally stable and easy to manufacture.

This object is achieved by the combination of features recited in claim 1.

Advantageous embodiments can be inferred from the subclaims. The invention is based on the knowledge that the problem of the lack of layer stability of ozone-sensitive layers can be solved by encapsulating ozone-sensitive materials in a polymer matrix or by applying a polymerizing coating or even a polymer layer. By encapsulating the materials in the polymer matrix, the agglomeration of water is reduced or in some cases totally prevented in spite of the often hygroscopic behavior of the ozone-sensitive materials, with the result that no instabilities of the sensor layer ensue. Even in the event of a possible local formation of water spots due to strongly hydrophilic salts, the layer is preserved as a result of the stabilizing effect of the polymers on the structure.

In addition to the stability function, a polymer matrix also has a protection function. The encapsulated compounds, the ozone-sensitive materials, are protected against various environmental effects by polymers or polymer mixtures. Such effects may be corrosive influences such as oxidizing ($NO_2$, $SO_2$) or reducing gases ($NH_3$) or other inactivating agents such as particles, for example dust or aerosols. This means that the polymer matrix takes on the function of a protective filter during gas detection, preserving or even improving the sensitivity to gas.

Owing to the structure-stabilizing effect of the polymers, it is also possible to use ozone-sensitive materials, for example salts, which previously could not be used as gas-sensitive layers due to the layer preparation difficulties associated with them. This means that it is also possible to develop new sensitive layers, such as using NaI, KClO$_3$ or KIO$_3$ for example.

As a result of the use of polymer matrices, the reversibility of the sensor reaction can be accelerated, leading to an improvement in sensor response times.

A further advantage with the polymer matrix acting as a filter lies in the possibility of making a selection of the analytes based on the selectivity and sensitivity of the sensor layer. If the gas-sensitive material is coated with a polymer layer or membrane, for example, this creates a filter effect, with the result that only certain gases come into contact with the sensitive material. By choosing the polymer it is possible, for example, to make a selection aimed at avoiding cross-sensitivities with other gases, so that gases such as H$_2$O, NO$_x$, SO$_2$, Cl$_2$ are filtered out. An increase in sensitivity is achieved because the gas reaction actually desired is no longer inhibited by cross-sensitivities.

Encapsulating halogenide salts in polymer matrices leads to an improvement in the preparation of the layer as a whole. Since polymers can be applied to surfaces using a variety of simple preparation techniques, process techniques such as spray film, spin coating or tampon printing can be used. This leads not only to a greater variety of preparation techniques, but also to cheaper sensor designs.

A polymer matrix can also be used selectively to compensate for the cross-sensitivity to interfering gases. The ozone-sensitive salt potassium iodide (KI), for example, is sensitive to humidity and generates a positive signal. A polymer is inversely sensitive to humidity, producing a correspondingly negative signal. It means that the signal of the interfering gas of the ozone-sensitive salt can be directly compensated for by the inverse signal of the polymer. Suitable adjustment of the proportions of the individual substances is necessary in order to precisely eliminate the cross-sensitivity. The layer can therefore be formed such that only the ozone signal is displayed even with different concentrations of humidity. Thus, a compensation of the interfering gases is possible directly by means of a polymer layer. Furthermore, the compensation of interfering gases can be effected by polymers which themselves act as ozone filters. In this way it is possible to determine only the sensor signal which is attributable to humidity or other interfering gases but not to an ozone reaction. Using this signal, the right ozone value can be determined compared with a non-ozone-filtered sensor signal.

BRIEF DESCRIPTION OF THE DRAWINGS

Exemplary embodiments that do not limit the invention are described in the following with reference to schematic figures.

DETAILED DESCRIPTION OF THE INVENTION

There are essentially two different forms of layer preparation for the purpose of ozone sensor production.

Figure 1:
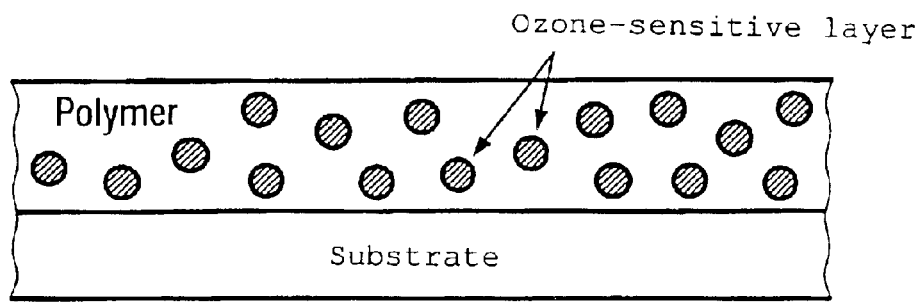
FIG. 1 shows a cross-section through a sensor design featuring a substrate and superimposed polymer layer with embedded particles of an ozone-sensitive material.

As shown in FIG. 1, a polymer and an ozone-sensitive material can be homogeneously mixed and applied to the surface of a substrate using a suitable preparation technique such as screen printing, spray film, tampon printing or spin coating. In FIG. 1, ozone-sensitive materials are shown distributed in a polymer layer. Here, while it is entirely possible for ozone-sensitive particles to be lying exposed at the surface, the major part is embedded in the polymer. The signal pickup of the sensor signal is performed at the externally recordable polymer layer, which changes its potential if the target gas is present. This so-called work function change is selected and evaluated.

Figure 2:
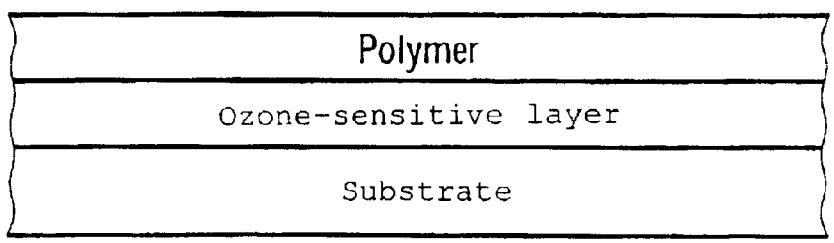
FIG. 2 shows an ozone sensor design featuring an ozone-sensitive layer and a polymer coating.

FIG. 2 shows another variant in which the layer preparation is carried out in such a way that the sensitive material is initially applied to the surface of the substrate by vapor deposition or spraying. The substrate is then covered by one or more polymer layers. The polymer layer completely covers the ozone-sensitive layer. The lateral ends of the layer do not come into contact with the gas, but are likewise covered by the polymer layer. Thus, the lateral area is also protected. The ground electrode is located at the rear of the sensitive layer, i.e. between sensitive layer and substrate.

A polymer matrix may exhibit no reaction to the presence of gas. However, by targeted selection of specific polymers it is possible to put together selective combinations of ozone-sensitive material and polymer matrix, where, as a result of a specific response by a polymer to an interfering gas, the interfering signal of the same interfering gas can be compensated for at the ozone-sensitive layer. Examples of specifically selected combinations of polymers and ozone-sensitive materials are described with reference to FIGS. 3 and 5. For example, polyimide reacts to an increase in humidity with a negative work function signal, KI in PMSS reacts to increased humidity with a positive work function signal and a positive signal to an increase in ozone. The humidity signal can be compensated for by the combination, for example polymer mixture.

A further variant is the combination of a humidity-sensitive metal salt such as CoCl$_2$ or CuCl$_2$ producing a negative work function signal, and an ozone-sensitive material such as KI or 12 producing a positive humidity signal, in a polymer matrix such as e.g. polyvinylpyrrolidone or cellulose.

Figure 4:
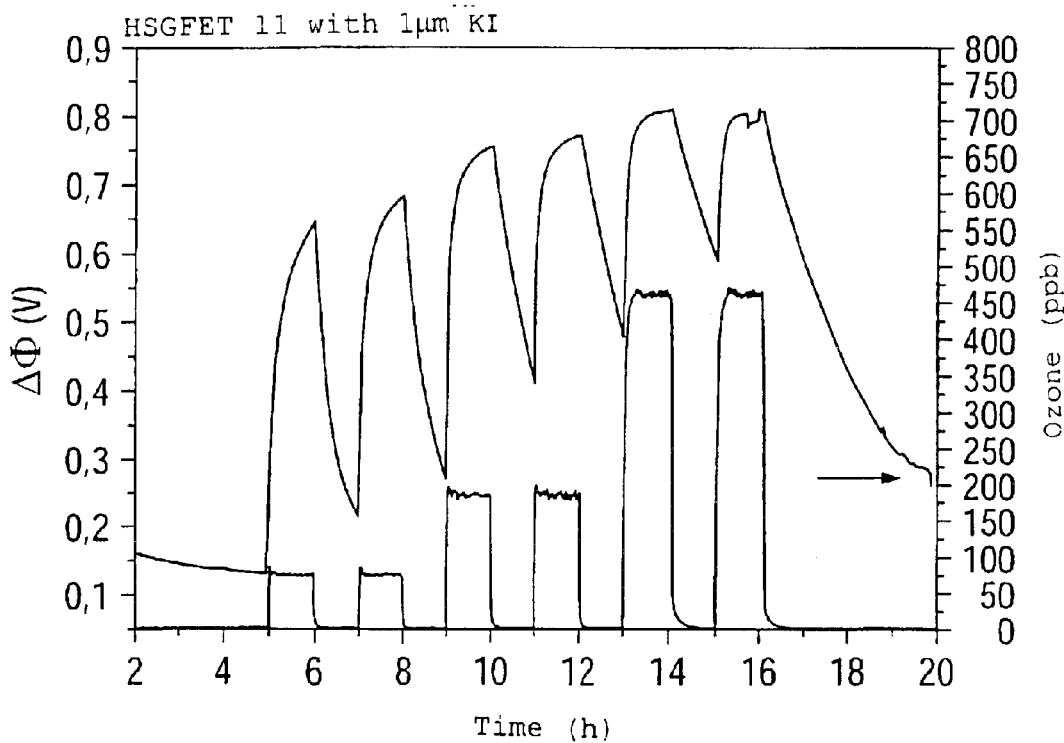
FIG. 4 shows ozone concentrations with associated sensor signal in the case of a sensor with pure potassium iodide layer.

FIG. 4 shows the signal waveform of a pure 1 $\mu$m-thick KI layer. This is applied to an HSG field effect transistor by means of a vapor deposition process. The ozone concentrations are incorporated in three stages, at 50, 175 and 475 ppb. The associated sensor signals plotted above them can be converted into corresponding ozone concentrations. However, the prior art exhibits significant disadvantages for the ozone-sensitive KI layer without additional stabilization by means of a protective layer according to the invention.

Figure 3:
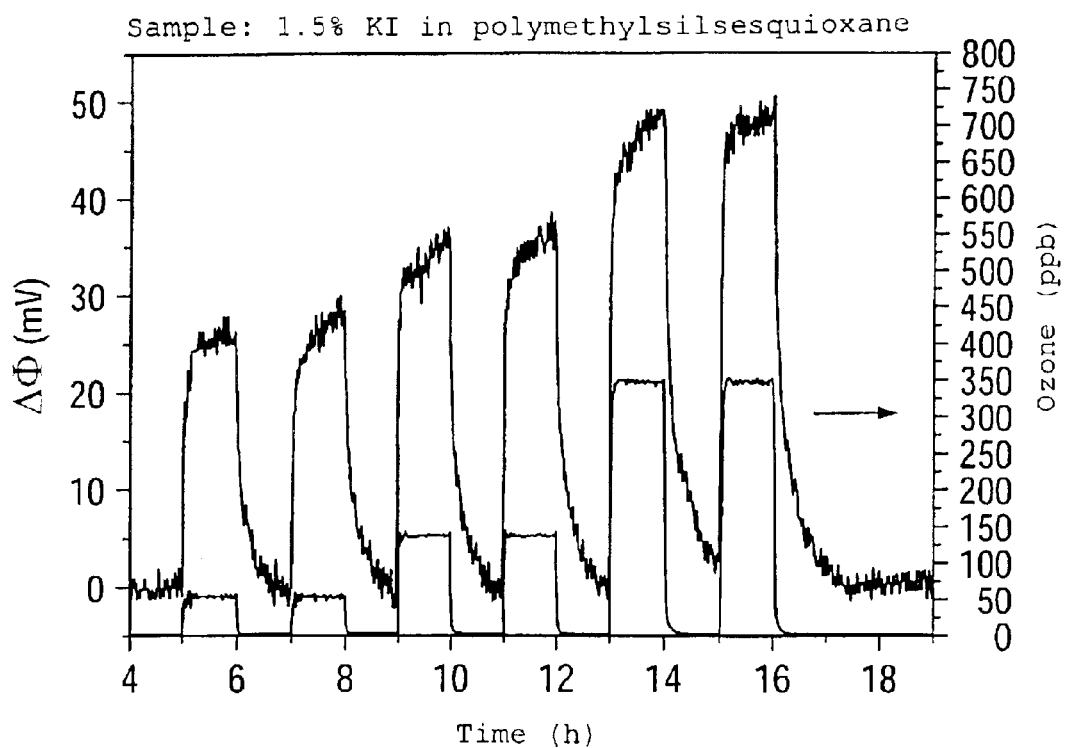
FIG. 3 shows ozone concentrations and associated ozone sensor signals in the case of an ozone-sensitive layer composed of PMSS containing 1.5% potassium iodide.

As shown in FIG. 3, ozone concentrations are incorporated in an ozone sensor in the stages 50, 100 and 300 ppb. The signal waveform at the ozone sensor is recorded above in each case in the form of the electrical sensor signal. The sensor according to FIG. 3 contains a polymer matrix composed of PMSS (polymethylsilsesquioxane) containing 1.5% (w/w) potassium iodide as an ozone-sensitive layer. By means of this combination it is possible to obtain an ozone sensor layer with a sensitivity of approx. 25 mV at 50 ppb ozone and approx. 50 mV at approx. 300 ppb. With the aid of this layer, the response time can thus be significantly reduced compared with a measurement with a pure KI layer without polymer as shown in FIG. 4.

Figure 5:
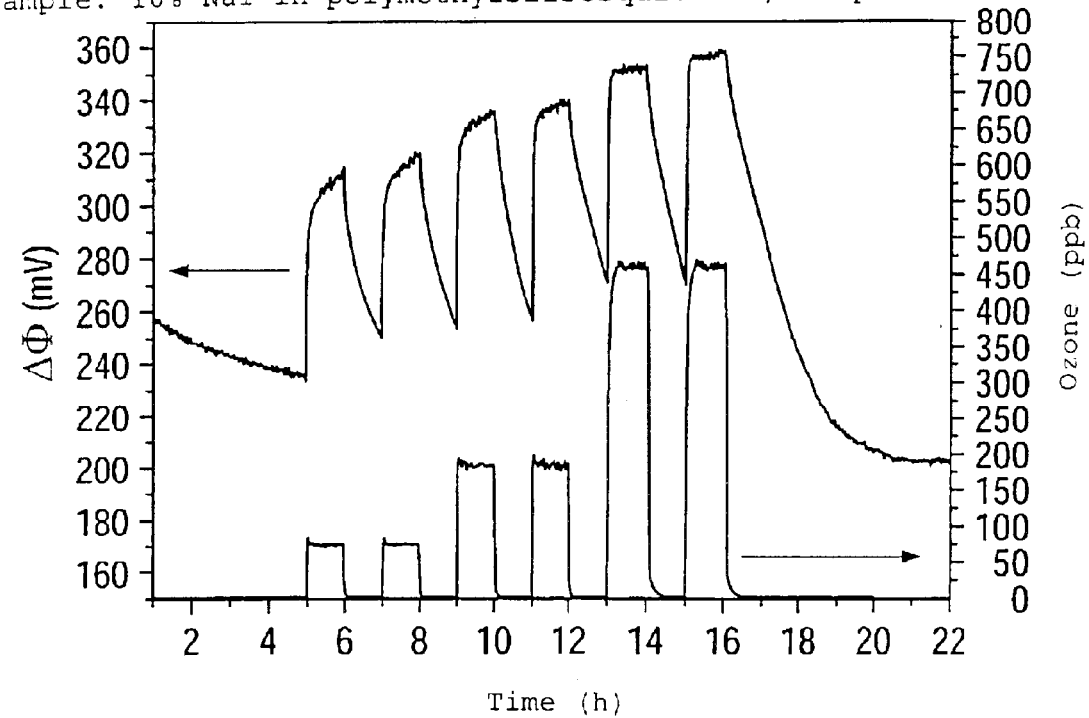
FIG. 5 shows a diagram with ozone concentrations and associated ozone sensor signals of a sensor having a PMSS layer containing 10% sodium iodide.

FIG. 5 shows similar three-stage ozone concentrations which are applied to a sensor, the sensor layer consisting of PMSS containing 10% (w/w) sodium iodide. A "dispersion" of the sodium iodide layer is prevented by means of the PMSS polymer. Thus, this halogenide salt is available for the first time as a sensitive layer for determining ozone, since the service life of the layer is sufficiently long. As a result of the faster response times of the sensor it also becomes clear that important layer properties can be improved through the use of the polymer matrix.

Figure 6:
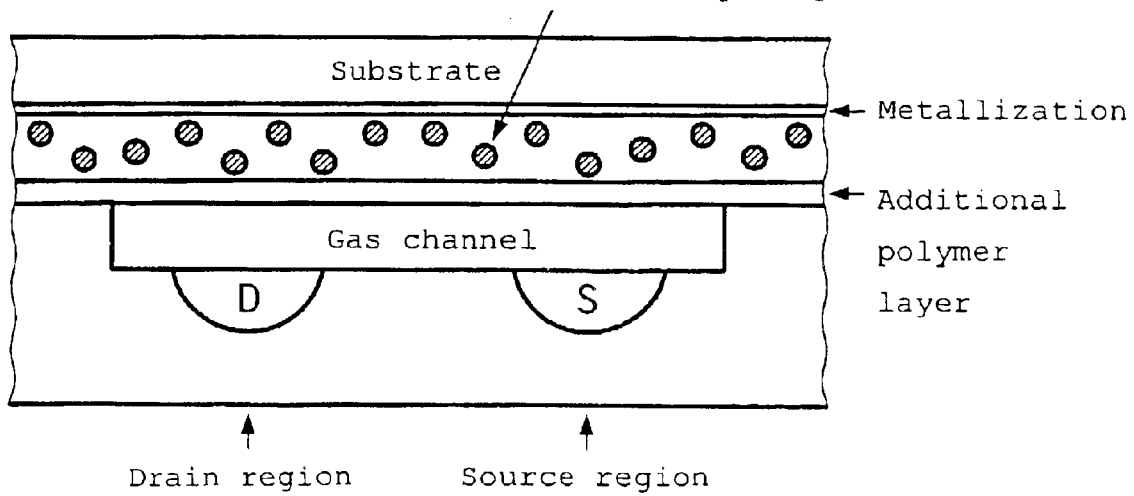
FIG. 6 shows a sectional view of a gas sensor which is represented as a field effect transistor for the purpose of reading out work function changes.

FIG. 6 shows a sectional view of a field effect transistor. This acts as a gas sensor and in particular as an ozone sensor. The gas mixture to be measured is offered to the sensor through the gas channel. In this illustration, the actual layer that is sensitive to a target gas is protected by a so-called additional polymer layer. The ozone-sensitive layer consists of a layer made up of a polymer or polymer mixture, in which gas-sensitive material is encapsulated. The particles are distributed preferably uniformly in the layer, as shown in the figure. Provided between ozone-sensitive layer and substrate is a metallization, which can represent a ground electrode.

The following publications are cited in this document:

[1] T. Doll, J. Lechner, I. Eisele, K.-D. Schierbaum, W. G öpel, "Ozone detection in the ppb range with work function sensors operating at room temperature", Sensors and Actuators B 34 (1996) 506–510

[2] A. Fuchs, "Ozonsensorik mit Feldeffekttransistoren", Institut für Physic, Fakultät für Elektrotechnik, Universit ät der Bundeswehr München, 1999 ("Ozone sensor systems using field effect transistors", Institute for Physics, Faculty of Electrical and Electronic Engineering, University of the German Federal Armed Forces Munich, 1999)

What is claimed is:

1. Ozone sensor, comprising:
at least one ozone-sensitive layer, the ozone-sensitive layer comprising one of
i) at least one ozone-sensitive material embedded in a polymer or polymer mixture and
ii) at least one ozone-sensitive material layer overlaid with a layer of at least one polymer or polymer mixture,
the ozone-sensitive layer configured with an externally recordable polymer layer providing a work function change signal that changes in correspondence with ozone concentration present at the ozone-sensitive layer according to the ozone concentration work function change principle,
wherein the polymer or polymer mixture is not the ozone-sensitive material.

2. Ozone sensor according to claim 1, wherein the ozone-sensitive material is a non-encapsulated halogenide compound embedded in a polymer mixture.

3. Ozone sensor according to claim 2, wherein the halogenide compound is an iodine compound.

4. Ozone sensor according to claim 2,
wherein the halogenide compound is a halogenide salt selected from the group consisting of NaI, KI, NaIO$_3$, KIO$_3$, NaClO$_3$, KClO$_3$, KCl, NaCl, NaBr, KBr, NaBrO$_3$, or KBrO$_3$.

5. Ozone sensor according to claim 1,
wherein the polymer or polymer mixture comprises a substance or a mixture from one of the following groups: polypyrrolidone, polyvinylpyrrolidone, polysiloxane, polysilsesquioxane, gelatine, polyimide, polymethacrylate, polyvinylcinnamate, polyamide or cellulose derivatives.

6. Ozone sensor according to claim 1,
wherein the ozone-sensitive material encapsulated in polymer or polymer mixtures is distributed in the layer in the form of particles.

7. Ozone sensor according to claim 1,
wherein the materials of the ozone-sensitive layer are selected such that cross-sensitivities of ozone-sensitive materials in combination with interfering gases are compensated by inverse sensitivities of the at least one polymer or polymer mixture.

8. Ozone sensor according to claim 1,
wherein the ozone-sensitive layer consists of the polymer polymethylsilsesquioxane (PMSS) containing 1.5% (w/w) potassium iodide (KI).

9. Ozone sensor according to claim 1,
wherein the ozone-sensitive layer consists of the polymer polymethylsilsesquioxane (PMSS) containing 10% (w/w) sodium iodide (NaI).

10. Ozone sensor according to claim 1,
wherein the polymer or polymer mixture represents an ozone filter, such that only interfering signals can be detected.

11. Ozone sensor according to claim 1,
wherein an ozone-sensitive layer implemented as a polymer matrix is coated with ozone-sensitive material by means of an additional polymer layer.

12. Ozone sensor according to claim 2,
wherein the polymer or polymer mixture comprises a substance or a mixture from one of the following groups: polypyrrolidone, polyvinylpyrrolidone, polysiloxane, polysilsesquioxane, gelatine, polyimide, polymethacrylate, polyvinylcinnamate, polyamide or cellulose derivatives.

13. Ozone sensor according to claim 2,
wherein the ozone-sensitive material encapsulated in polymer or polymer mixtures is distributed in the layer in the form of particles.

14. Ozone sensor according to claim 2,
wherein the materials of the ozone-sensitive layer are selected such that cross-sensitivites of ozone-sensitive materials in combination with interfering gases are compensated by inverse sensitivities of the at least one polymer or polymer mixture.

15. Ozone sensor according to claim 5,
wherein the ozone-sensitive layer consists of the polymer polymethylsilsesquioxane (PMSS) containing 1.5% (w/w) potassium iodide (KI).

16. Ozone sensor according to claim 6,
wherein the ozone-sensitive layer consists of the polymer polymethylsilsesquioxane (PMSS) containing 1.5% (w/w) potassium iodide (KI).

17. Ozone sensor according to claim 7,
wherein the ozone-sensitive layer consists of the polymer polymethylsilsesquioxane (PMSS) containing 1.5% (w/w) potassium iodide (KI).

18. Ozone sensor according to claim 5,
wherein the ozone-sensitive layer consists of the polymer polymethylsilsesquioxane (PMSS) containing 10% (w/w) sodium iodide (NaI).

19. Ozone sensor according to claim 6,
wherein the ozone-sensitive layer consists of the polymer polymethylsilsesquioxane (PMSS) containing 10% (w/w) sodium iodide (NaI).

20. Ozone sensor according to claim 7,
wherein the ozone-sensitive layer consists of the polymer polymethylsilsesquioxane (PMSS) containing 10% (w/w) sodium iodide (NaI).

21. Ozone sensor according to claim 1,
wherein the work function change signal, that changes in correspondence with ozone concentration present at the ozone-sensitive material according to the ozone concentration present work function change principle, is an electrical potential signal.

22. Ozone sensor according to claim 21,
wherein the ozone-sensitive material does not have dimensional shape stability, the ozone-sensitive material being embedded in one of a polymer and a polymer mixture that shape stabilizes the ozone-sensitive layer.

23. The ozone sensor of claim 1,
wherein the sensor is in the formed of a field effect transistor comprising a gas channel adjacent a drain region and a source region and providing a gas mixture path through an interior of the sensor, the gas channel separating the ozone-sensitive layer from the drain region and the source region.

* * * * *